United States Patent [19]

Lysenko et al.

[11] 4,435,573
[45] Mar. 6, 1984

[54] PROCESS FOR THE PREPARATION OF SUBSTITUTED PYRIDINES

[75] Inventors: Zenon Lysenko; Richard G. Pews, both of Midland, Mich.

[73] Assignee: The Dow Chemical Company, Midland, Mich.

[21] Appl. No.: 436,231

[22] Filed: Oct. 25, 1982

[51] Int. Cl.³ .......................................... C07D 213/09
[52] U.S. Cl. ................................................... 546/250
[58] Field of Search ........................................ 546/250

[56] References Cited
FOREIGN PATENT DOCUMENTS
46735  3/1982  European Pat. Off. ............ 546/250

Primary Examiner—Robert T. Bond

[57] ABSTRACT

Substituted pyridines are prepared by the base and transition metal catalyzed ring closure of substituted 5-oxo-pentane-1-nitriles.

8 Claims, No Drawings

PROCESS FOR THE PREPARATION OF SUBSTITUTED PYRIDINES

BACKGROUND OF THE INVENTION

This invention relates to the preparation of substituted pyridines by a base and transition metal catalyzed ring closure of substituted 5-oxo-pentane-1-nitriles.

DESCRIPTION OF THE PRIOR ART

U.S. Pat. No. 4,294,968 discloses the preparation of α-picoline from 5-oxohexanenitrile using a dehydrogenation catalyst such as carbon-supported palladium.

U.S. Pat. No. 3,007,931 teaches the ring closure of, for example, 4-cyanobutyraldehyde using dehydrogenation catalysts.

U.S. Pat. No. 4,337,342 teaches the preparation of 3-picoline from acetaldehyde and/or crotonaldehyde and formaldehyde in the presence of an ammonium salt.

U.S. Pat. No. 2,719,159 teaches the preparation of pyridine compounds from glutaric dialdehydes in the presence of oxidizing agents and ammonium salts.

British Pat. No. 1,304,155 teaches the preparation of C-substituted pyridines and/or hydrogenated C-substituted pyridines from gamma-cyanoketones in the gaseous state in the presence of hydrogen with a catalyst system which contains a metal from the group copper, silver, gold, iron, nickel, cobalt and the platinum group.

European Patent application No. 46735 teaches the preparation of chloropyridines substituted by methyl, trichloromethyl or trifluoromethyl groups by adding the appropriate aldehyde to acrylonitrile, methacylonitrile or α-trifluoromethacrylonitrile in the presence of a catalyst and cyclizing the resulting intermediate in the presence of hydrogen chloride or a substance which forms hydrogen chloride under the reaction conditions.

SUMMARY OF THE INVENTION

This invention provides a process for preparing compounds having the formula

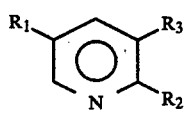

wherein $R_1$ is alkyl, preferably $C_1$-$C_4$ alkyl, aryl, preferably phenyl, hydrogen or halogen, preferably Cl, Br or F, $R_2$ is Cl or Br and $R_3$ is Cl, Br or F, which comprises cyclizing a compound having the formula

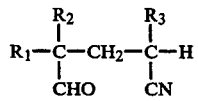

wherein $R_1$, $R_2$ and $R_3$ are as above-defined, in the presence of a catalytic amount of at least one organic base and/or an organometallic catalyst.

The compounds prepared by the process of this invention are advantageously employed as intermediates in the preparation of compounds having insecticidal and/or herbicidal activity as described, for example, in European Patent Application No. 46735.

DETAILED DESCRIPTION OF THE INVENTION

The reaction may be carried out at any temperature from about room temperature, e.g., 25° C., to 250° C., but is preferably carried out at temperatures of 70° to 250° C. and most preferably at temperatures of about 200° to 220° C.

Any organic base such as, for example, ethylamine, methylamine and cyclohexylamine may be employed, although isopropylamine is preferred.

The organometallic catalyst may be any transition metal catalyst, such as, for example, Ni(Cl$_2$) or CoCl$_2$($\phi_3$P)$_2$. The preferred catalyst is nickel dichlorobis(triphenylphosphine). The reaction is advantageously carried out in a suitable inert polar solvent, preferably a nitrile solvent and most preferably acetonitrile.

The invention is further illustrated by the following examples.

EXAMPLE 1

Preparation of 2,3-dichloro-5-methylpyridine

A solution of 32.343 grams of 2,4-dichloro-4-methyl-5-oxopentanenitrile in 150 ml of acetonitrile and containing 300 mg of nickel dichlorobis(triphenylphosphine) was pumped through a nickel coil having a volume of about 30 ml at the rate of 2.0-2.5 ml/minute. The solution had been preheated to 200°-210° C. at a pressure of 250 psig.

Gas chromatographic (G.C.) analysis showed 90% conversion of aldehyde with a 77% yield of 2,3-dichloro-5-methylpyridine.

EXAMPLE 2

The above experiment was repeated except that 30.908 grams of the oxonitrile were used and 3 ml of isopropylamine were included in the solution in addition to the nickel catalyst. Analysis by G.C. showed a conversion of 94.3% and a yield of 23.9 grams (90.1%).

EXAMPLE 3

The above experiment was repeated except that 31.7 grams of oxonitrile were used and about 1% by weight (3.1) of isopropylamine was employed as the sole catalyst. The yield was 80% by G.C.

EXAMPLE 4

A solution of 32.1 grams of 2,4-dichloro-4-methyl-5-oxopentanenitrile in 250 ml of acetonitrile containing 3 ml of isopropylamine and about 300 mg of nickel dichlorobis(triphenylphosphine) was heated to reflux for 48 hours. The excess acetontrile was then removed by vacuum distillation and the residue flask-distilled at 85°-90° C. at 5 mm Hg on a Kugelrohr. The yield was 27.0 grams of 2,3-dichloro-5-methylpyridine (86%) isolated as a white solid.

We claim:

1. A process for preparing a compound having the formula

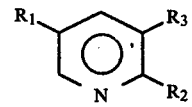

wherein $R_1$ is $C_1$–$C_4$ alkyl, phenyl, hydrogen or halogen, $R_2$ is Cl or Br and $R_3$ is Cl, Br or F which comprises cyclizing a compound having the formula

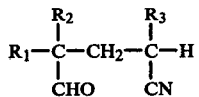

wherein $R_1$, $R_2$ and $R_3$ are as above-defined, in the presence of a catalytic amount of at least one organic amine base and/or an organometallic transition metal catalyst.

2. Process of claim 1 wherein $R_1$ is methyl, and $R_2$ and $R_3$ are Cl.

3. Process of claim 1 wherein $R_1$ is ethyl and $R_2$ and $R_3$ are Cl.

4. Process of claim 1 wherein the organic base is isopropylamine.

5. Process of claim 2 wherein the catalyst is nickel dichlorobis(triphenylphosphine).

6. Process of claim 1 wherein the reaction is carried out at a temperature of 25° to 250° C.

7. Process of claim 5 wherein the temperature is 70° to 250° C.

8. Process of claim 1 wherein the catalyst comprises an organic amine and nickel dichlorobis(triphenylphosphine).

* * * * *

UNITED STATES PATENT AND TRADEMARK OFFICE
CERTIFICATE OF CORRECTION

PATENT NO. : 4,435,573

DATED : March 6, 1984

INVENTOR(S) : Zenon Lysenko et al.

It is certified that error appears in the above—identified patent and that said Letters Patent is hereby corrected as shown below:

Col. 2, line 46, "(3.1)" should read --(3.1 g)--.

Col. 2, line 54, "acetontrile" should read --acetonitrile--.

Signed and Sealed this

Second Day of October 1984

[SEAL]

Attest:

GERALD J. MOSSINGHOFF

Attesting Officer    Commissioner of Patents and Trademarks